United States Patent [19]

Oswald et al.

[11] 4,310,471

[45] Jan. 12, 1982

[54] ALKYL ARYL SULFONATE ESTERS

[75] Inventors: Alexis A. Oswald, Mountainside; Edmund J. Mozeleski, North Plainfield, both of N.J.

[73] Assignee: Exxon Research & Engineering Co., Florham Park, N.J.

[21] Appl. No.: 125,501

[22] Filed: Feb. 28, 1980

Related U.S. Application Data

[63] Continuation of Ser. No. 935,610, Aug. 21, 1978, abandoned.

[51] Int. Cl.$^3$ ............... C07C 141/00; B01F 17/02
[52] U.S. Cl. ............... 260/456 P; 252/353
[58] Field of Search ............... 260/456 P

[56] References Cited

U.S. PATENT DOCUMENTS 3,206,492  9/1965  Turbak ............... 260/456

FOREIGN PATENT DOCUMENTS 554262  3/1958  Canada ............... 260/456 P
673842  6/1952  United Kingdom ............... 260/456 P

OTHER PUBLICATIONS

Chem. Abst. Yoshinori 79678f vol. 81 (1974).

*Primary Examiner*—Alan Siegel
*Attorney, Agent, or Firm*—Jerome E. Luecke; James H. Takemoto

[57] ABSTRACT

Salts of surfactant alkyl aromatic sulfonic acids react with lower dialkyl sulfates under anhydrous conditions to form the corresponding novel lower alkyl sulfonate esters and as by-products, the salts of the corresponding alkyl sulfuric acid.

3 Claims, No Drawings

ALKYL ARYL SULFONATE ESTERS

This is a continuation, of application Ser. No. 935,610, filed Aug. 21, 1978 now abandoned.

BACKGROUND OF THE INVENTION

2. Field of the Invention

This invention relates to novel, lower alkyl ester derivatives of aromatic sulfonic acids of surfactant character and the preparation of lower alkyl esters of alkylated aromatic and aliphatic sulfonic acids. A subclass of these compounds, which is of particular interest, consists of alkylated benzene sulfonic acid methyl esters. Another aspect of the invention is concerned with the preparation of the sulfonate esters of the present invention via the alkylation of the corresponding sulfonate salts with dialkyl sulfates, particularly dimethyl sulfate. A further feature of this aspect is the isolation of the novel sulfonate esters by extraction, distillation and crystallization.

2. Description of the Prior Art

Lower alkyl esters of aliphatic, aromatic and alkyl substituted aromatic sulfonic acids are described in the art. For example, information relating to the aforesaid compositions is disclosed in U.S. Pat. No. 2,017,803; British Pat. No. 669,592; U.S. Pat. Nos. 3,206,492; 2,831,013; 3,818,102; 3,853,939; 3,882,238; 3,301,886; French Pat. No. 987,054 (abstract in Chemical Abstracts Volume 50, column 7139); U.S. Pat. No. 2,613,195; "Surface Active Agents and Detergents" Volume 2, page 87, Schwartz et al, Interscience Publishers (1958); French Pat. No. 940,088 (abstracted in Chemical Abstracts Volume 1950, column 7353); British Pat. No. 673,842 (abstracted in Chemical Abstracts Volume 46, column 11724); Japanese Pat. No. 73 40, 737 (abstracted in Chemical Abstracts Volume 8179678f); British Pat. No. 673,842; and British Journal of Industrial Medicine, Vol. 10, pp. 121-124 (1954).

J. S. Showell, J. R. Russell and D. Swern described the synthesis of $C_{12}$ to $C_{18}$ alkane sulfonic acid methyl ester by reacting the corresponding acids with diazomethane. For reference, see J. Org. Chem. Vol. 27, pages 2853 to 2858, 1962. A. Nersarian and P. R. Johnson prepared the $C_1$ to $C_4$ alkyl esters of dodecane sulfonic acid and the methyl ester of chlorosulfonated polyethylenes from the corresponding sulfonic acid silver salts and alkyl iodides according to W. D. Emmons and A. F. Ferris. See J. Appl. Polymer Sci., Vol. 9, pages 1653 to 1668, 1965 and J. Am. Chem. Soc., Vol. 75, page 2257, 1978. Straus et al in U.S. Pat. No. 3,875,102 discloses the synthesis of the methyl esters of oligomers of detergent sulfonic acids by reacting the oligomeric acids with diazomethane.

The synthesis of lower alkyl, particularly methyl esters of sulfonic acids is a much studied reaction. Metzger et al in U.S. Pat. No. 3,301,886 (cited above) disclose the synthesis of lower alkyl esters of aromatic sulfonic acids, including esters of i-dodecylbenzene sulfonic acid, by reacting metal salts of the corresponding acids with dialkyl sulfates in the presence of a base, preferably sodium bicarbonate. The preparation of such esters from the corresponding sulfonic acid sodium salts via alkylation with dimethyl sulfate generally at temperatures above 150° C. was studied by several workers: F. Ullmann, Ann. der Chemie, 327, 117 (1903); A. Werner, ibid. 321, 269 (1902); P. Ruggli and E. Peyer, Helv. Chim. Acta 9, 939, 946, 948 (1926); H. J. Barber et al, J. Appl. Chem. (London) 3, 253-265 (1953). Free sulfonic acids could be methylated at about 80° using a highly reactive derivative of dimethyl sulfate and dimethyl formamide as disclosed by C. W. Schroeck in U.S. Pat. No. 3,956,354. The same patent also discloses a similar reaction of sulfonic acids with triethyl phosphate.

Another frequently used method, applicable to the synthesis of aromatic sulfonic acid esters, employs the reaction of the corresponding aromatic hydrocarbons with methyl or ethyl chlorosulfonate: F. W. Bushong, Am. Chem. J. 30, 212-224 (1930); M. Frerejacque, Ann. der Chimie, 14 (10) 147-226 (1930); and the above cited article by Cruikshank et al. Finally, the reaction of the corresponding sulfonic acid chlorides with alcohols in the presence of acid binding agents is also generally applicable for the synthesis of the prior art compositions: W. Rodionow, Bull. Soc. Chim. 39 (4), 305-325 (1926); V. C. Sekera and C. S. Marvel, J. Am. Chem. Soc. 55, 345-349 (1933); B. L. Emling, ibid. 74, 4703-4704 (1952). The esters of 4-toluene sulfonic acid were studied as plasticizers for nitrocellulose lacquers by A. Kraus, Arbeitsgemeinschaft Farben and Lacke, Nos. 5 and 6, 27-28 (1943).

SUMMARY OF THE INVENTION

In accordance with the present invention, it has been discovered that lower alkyl esters of long chain alkyl substituted aromatic sulfonic acids can be readily prepared in high yield through the reaction of a salt of said acid with a dialkyl sulfate carried out in the presence of a diluent under substantially anhydrous conditions. The lower alkyl sulfonate esters are thermally and hydrolytically stable. The compositions of the present have utility as surfactants or surfactant intermediates. Further, the higher alkyl substituted aromatic sulfonate esters can be readily employed in the preparation of liquid crystal materials whereas compositions such as dodecylbenzene substituted aromatic sulfonate esters do not readily form liquid crystal compositions.

The compositions of the present invention are lower alkyl esters of surfactant sulfonic acids. As such they can be characterized by the general formula

$$R_b Ar(SO_3 R')_p$$

wherein R is a higher aliphatic group, preferably a $C_9$ to $C_{50}$ aliphatic radical, more preferably a $C_9$ to $C_{50}$ unsubstituted or substituted aliphatic hydrocarbyl radical, most preferably such a radical is selected from the group consisting of open chain alkyl, alkylcycloalkyl, alkenyl and hydroxyalkenyl groups; Ar is an aromatic radical preferably having carbons in the $C_6$ to $C_{12}$ range, more preferably an unsubstituted or substituted aromatic hydrocarbyl radical, most preferably selected from radicals derived from benzene, toluene, xylene, diphenyl oxide and naphthalene; R' is a $C_1$ to $C_4$ alkyl, preferably primary alkyl, more preferably $C_1$ to $C_2$ alkyl, most preferably 1; b and p are numbers ranging from 1 to 5, preferably 1-2, more preferably 1 with the proviso that if R is the only aliphatic substituent of a benzene ring, and b equals 1, it is a $C_{15}$ to $C_{50}$, preferably $C_{21}$ to $C_{50}$ aliphatic group.

The R aliphatic hydrocarbyl radical can be substituted preferably monosubstituted with hydroxy, chloro, $C_1$ to $C_{18}$ carboalkoxy, $C_1$ to $C_{18}$ alkyloxy and alkylthio radicals. They can be also interrupted with amido, carbonyl, carboxylic ester, ether oxygen and or sulfur. These aliphatic "interrupting" groups can be also present as "bridging" groups between the aliphatic R and aromatic Ar moieties. The same groups, preferably oxygen, can also interrupt two rings of an aromatic radical.

The Ar aromatic hydrocarbyl radical can be substituted with up to 4 preferably up to 2 radicals, more preferably with radical selected from the group consisting of $C_1$ to $C_4$ alkyl and halogen, most preferably with methyl and chlorine.

The carbon range of the R aliphatic radical is 9 to 50, preferably 13 to 40, more preferably 15 to 30. It is preferred that the sum of the number of aromatic and aliphatic carbons be a minimum of 19. The carbon range of the Ar aromatic radical is 6 to 12, preferably 6 to 10, more preferably 6 to 8.

The aliphatic R' groups can be straight or branched chain alkyl, alkyl cycloalkyl. They can be saturated or unsaturated. However, saturated alkyl or mono-unsaturated alkenyl groups are preferred. Among the substituted aliphatic groups, hydroxyalkenyl groups are preferred. Saturated alkyl groups are most preferred.

The branched saturated higher alkyl groups, i.e., i-alkyl groups, may have short, $C_1$ to $C_3$ branches, such as those derived via propylene and i-butylene oligomerization. Other higher alkyl groups may possess longer $C_4$ to $C_{30}$ straight alkyl branches. The latter groups are preferably bound to aromatic groups to form linear alkyl aromatic moieties.

The aromatic groups can be benzenoid such as those derived from benzene, toluene, xylene, mesitylene, ethylbenzene, chlorobenzene. Another type of aromatic group possesses fused rings such as naphthalene, tetrahydronaphthalene, chloronaphthalene. In still another case, two or more benzenoid groups are bridged or directly linked by covalent bonds, e.g., in the case of diphenyl ether, diphenyl sulfide, biphenyl.

Also contemplated by the present invention are compositions comprising a mixture of monoalkyl benzene sulfonate esters, which mixtures comprise esters whose alkyl substituents substituted to a benzene ring are of differing carbon chain length. The preferred ester mixtures each fall within the provisions of the general formula $$RAr(SO_3R')_p$$

wherein Ar is benzene; R' is as defined above; p is as defined above; R is a $C_9$-$C_{50}$ aliphatic group and wherein the weighted average chain length of the R groups of the esters in the mixture, as determined by mass spectroscopy analysis and/or glc analysis of the alkyl benzene or/and olefin precursor, is 13 or greater, preferably 15 or greater. Such mixtures preferably contain less than 80 wt. % of a sulfonate ester substituted with a single higher alkyl substituent.

Preferred classes of monoalkyl benzene sulfonates are the normal (n)-alkyl sulfonates depicted hereinbelow

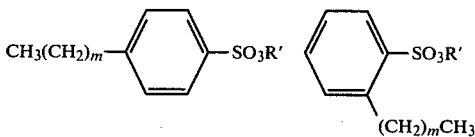

wherein m is 9 to 50, preferably 14 to 49, more preferably 20 to 29 and the linear (l) and iso (i) alkyl benzene sulfonate esters shown below

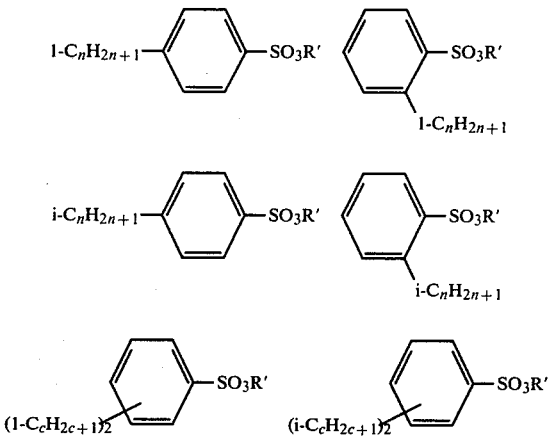

wherein n is 15 to 50, preferably 21 to 50; c is 9 to 50 and R' is $C_1$ to $C_4$ alkyl group. It should be noted that the distinction between ortho and para isomers and between compounds substituted by higher iso and linear alkyl groups is based on unexpectedly different properties. Such distinct esters also lead to surfactants having different solubility, biodegradability and surface activity. Other useful compounds include the monoalkyl toluene and monoalkyl xylene sulfonate esters below

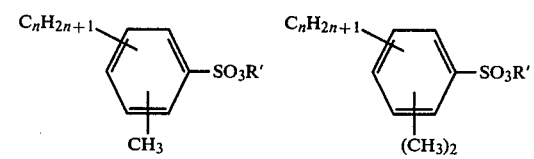

wherein n is 9 to 50 and R' is $C_1$ to $C_4$ alkyl group.

Another preferred type consists of alkyl naphthalene sulfonate esters

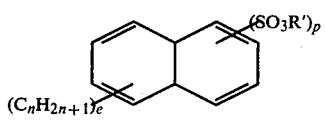

wherein e is 1 to 3 preferably 2, p is 1 to 3, preferably 1 or 2, n is 9 to 50 and R' is a $C_1$ to $C_4$ alkyl group.

Another type is the alkyl diphenyl ether sulfonates

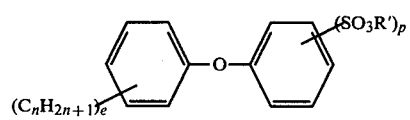

wherein e is 1 to 3, preferably 1, p is 1 to 3 preferably 2, n is 9 to 50 and R' is a $C_1$ to $C_4$ alkyl group.

Exemplary lower alkyl sulfonate esters of surfactant sulfonic acids are the following: ethyl octadecene sulfonate, methyl hydroxyhexadecene sulfonate, methyl l-dodecyl toluene sulfonate, methyl i-nonyl xylene sulfonate, methyl i-dodecyl mesitylene sulfonate, methyl l-octadecyl xylene sulfonate, methyl hexatriacontyl chlorobenzene sulfonate, methyl di-l-dodecyl toluene sulfonate, ethyl i-nonyl naphthalene sulfonate, methyl di-i-nonyl naphthalene sulfonate, dimethyl i-nonyl naphthalene disulfonate, dimethyl i-dodecyl diphenyl ether disulfonate, methyl n-dodecyl thiophene sulfonate, etc.

Exemplary surfactant alkyl substituted aromatic sulfonic acids are derived by sulfonation from alkylates. Alkylates are produced by reacting either linear or α- or branched (iso-) olefin mixtures of a certain carbon range with aromatic hydrocarbons preferably selected from the group consisting of benzene, toluene, mesitylene and naphthalene in the presence of an acid catalyst.

The lower alkyl esters of alkyl substituted aromatic sulfonic acids, i.e., the compounds of the present invention are advantageously derived by a process comprising reacting a salt of the sulfonic acid, selected from the group consisting of metal, quaternary ammonium and phosphonium salts, with a lower dialkyl sulfate. As it is shown by the reaction scheme, the by-product of such a process is the corresponding salt of a lower alkyl sulfuric acid.

$$R_bAr(SO_3M)_p + p(R'O)_2SO_2 \rightarrow R_bAr(SO_3R')_p + p\text{-}R'OSO_2M$$

On the formulae of the scheme, M stands for a moiety selected from the group consisting of a metal, a quaternary ammonium or a quaternary phosphonium and R, Ar, R', b and p are as previously defined with reference to the formula $R_b(Ar(SO_3R')_p$. Metal cations are preferred, particularly those of alkali and alkali earth metals such as sodium, potassium, calcium, magnesium. The quaternary cations are preferably those having lower alkyl, i.e., $C_1$ to $C_4$ alkyl, substituents. They are exemplified by tetramethyl phosphonium, tetraphenyl phosphonium, tetrabutyl ammonium, tetraethyl ammonium, tributyl methyl ammonium.

The exemplary alkyl aromatic surfactant sulfonic acid salt reactants possess structures analogous to those of the corresponding lower alkyl sulfonate ester products. These structures were discussed and exemplified earlier. The structural preferences are as discussed.

The lower dialkyl sulfate alkylating reagents preferably possess primary alkyl groups, such as primary i-butyl and n-propyl. The more preferred groups are methyl and ethyl. Di-methyl sulfate is the most preferred reagent.

The present process is preferably conducted under substantially anhydrous conditions, that is, the reaction mixture preferably contains less than about 10 ppm water. In the case of technical sulfonate salt reactants, it is preferred to remove all free and hydrate water. Anhydrous sulfonate salts, which are critical for substantially quantitative reactions, are most preferably obtained by removing such water at atmospheric pressure via co-distillation with xylene.

The reaction of the present process is carried out in the presence of inert liquid diluents which dissolve significant amounts of the reactants at the reaction temperature. Such diluents are preferably hydrocarbons and substituted hydrocarbons. Aromatic, substituted aromatic, particularly alkyl and chlorine substituted aromatic compounds are preferred. The aromatics are preferably benzenoid in character. The most preferred diluents are toluene and xylenes. Exemplary diluents are dodecane, dodecyl benzene, tetrahydronaphthalene, dodecyl cyclohexane, octadecene, biphenyl, diphenyl ether, mesitylene.

The present process is carried out at temperatures assuring fast reaction rates, reactant and product stability and efficient mixing. The reaction temperature is preferably in the range of 110°–145° C., more preferably 135°–145° C. Furthermore, additional base reagents as discussed in U.S. Pat. No. 3,206,492 are not required in the reaction zone and, accordingly, the ester formation reaction is preferably conducted in the absence of additional base reagents.

It is preferred to add the dialkyl sulfate reactant to the sulfonate salt, slowly at the reaction temperature. This procedure will avoid mixing problems due to intermediate gel formation. To complete the reaction, stirring and heating of the mixture is continued after the addition of the dialkyl sulfate. In the absence of reactive impurities, one can employ one mole of dialkyl sulfate per sulfonate salt equivalent. However, preferred amounts of the dialkyl sulfate range from 105% to 150% of the calculated value. Thus a complete reaction of the sulfonate salt is preferably assured.

The reaction mixture can be filtered to obtain the sulfonate ester products in the filtrate. The sulfuric acid monoester salt by-products are usually crystalline compounds, insoluble in the reaction mixture at room temperature. An alternative method for separating the products from the by-products employs selective extraction or dissolution. The ester products are normally soluble in liquids of low polarity such as hydrocarbons and chlorinated hydrocarbons. Low molecular weight alkanes and cycloalkanes having 3 to 6 carbons are preferred. The salt by-products are soluble in highly polar liquids such as water and/or methanol.

Solutions of the sulfonate esters can be purified by solvent extraction with aqueous sodium bicarbonate. The neutral sulfonate esters can be readily separated from their hydrocarbon precursors by selective adsorption on polar solids such as clay. Ortho and para isomers in the alkyl benzene sulfonate ester series can be separated by fractional crystallization.

The neutral methyl esters exhibit a remarkable thermal stability and can be generally purified via distillation in vacuo. Acid impurities, present before distillation or formed during distillation, can be advantageously neutralized by anhydrous, inorganic bases such as calcium oxide.

As highly stable and polar nonvolatile esters, lower alkyl esters of the present surfactant sulfonic acids are plasticizers.

The properties of these sulfonate esters are uniquely useful in the purification and characterization of sulfonate surfactants.

In the mass spectroscope, the present linear- and isoalkyl benzene sulfonic acid methyl esters undergo a different type of a fragmentation. The main primary ion fragments are the following:

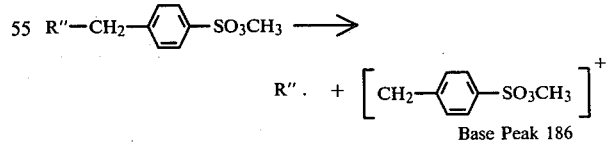

Base Peak 186

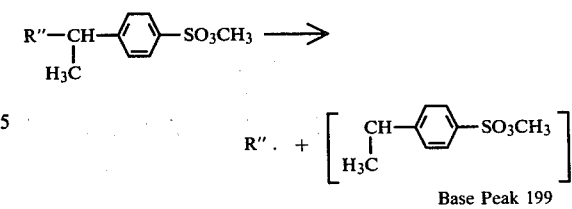

Base Peak 199

-continued

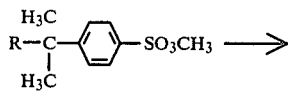 →

R". + 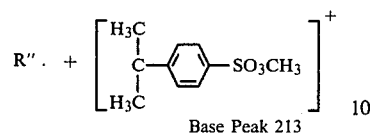

Base Peak 213

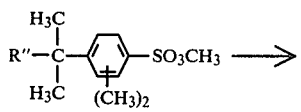 →

R". + 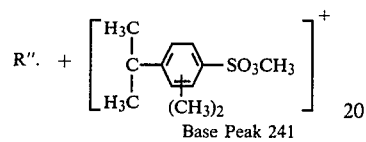

Base Peak 241 wherein R" is a higher alkyl group.

In contrast, methyl 4-n-dodecyl benzene sulfonate underwent fragmentation providing a desulfonated main fragment.

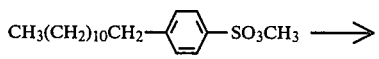 →

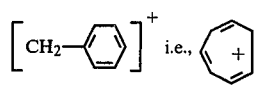

Base Peak 91

The fragmentation pattern of the higher alkyl groups formed in the mass spectrometer on the primary splitting of the 1- and i-alkyl benzene sulfonate esters is similar to those of the higher alkyl benzenes. Accordingly, the structure of surfactant alkyl arene sulfonate salts can be determined via conversion to the present sulfonate esters rather than via desulfonation.

The present sulfonate esters are highly reactive compounds having outstanding alkylating ability. They can be readily converted to pure anionic sulfonate surfactants, e.g., via the following reactions:

$$R_bAr\ [SO_3R']_p \xrightarrow{p\ NH_3} R_bAr\ [SO_3{}^-]_p\ [R'\overset{+}{N}H_3]_p$$

$$R_bAr\ [SO_3R']_p \xrightarrow{KI} R_bAr\ [SO_3K]_p + R'I$$

As stable, nonhygroscopic, nonvolatile, mobile liquids, the present sulfonate esters are conveniently stored and transported until they are converted to surfactants at or close to the site of their use.

The specific optimum structures of the present sulfonates mainly depend on the surfactant uses of their derivatives. For the preparation of aqueous detergents, shampoos and the like, the low molecular weight intermediates are preferred. For the manufacture of hydrocarbon soluble oil additives, the high molecular weight range compounds are preferred. However, in both of these areas homologous and isomeric mixtures of certain types of sulfonates are preferably utilized in the surfactant industry. In effect the application properties of such mixtures are superior to pure, single compounds of the same type.

Certain types of the present esters exhibit specific unexpected properties. Benzenoid esters having their sulfonate group in ortho-position relative to at least one alkyl group lead to surfactants having improved salt tolerance and tendency to form liquid crystals. The naphthalene sulfonate derivatives possess outstandingly high viscosities.

DESCRIPTION OF THE PREFERRED EMBODIMENTS

A summary of the conversion and the products produced in Examples 1 to 7 is provided in Tables I and II. Some of these experiments start with the conversion of the sulfonic acids or their hydroxyethylammonium salts to the appropriate sodium salts. Such conversions are also described.

TABLE I

Yield, Physical and Analytical Data of Methyl Higher i-Alkyl o-Xylene Sulfonate Esters $$i\text{-}C_nH_{2n}\text{-}\underset{\underset{H_3C\ \ \ CH_3}{}}{\bigcirc}\text{-}SO_3Na + (CH_3O)_2SO_2 \longrightarrow i\text{-}C_nH_{2n+1}\text{-}\underset{\underset{H_3C\ \ \ CH_3}{}}{\bigcirc}\text{-}SO_3CH_3 + CH_3OSO_3Na$$

| Ex. No. | Alkyl Carbon No. n | Summary Formula | Molecular Weight Calcd. | Molecular Weight Found | Dist. Yield,% | Boiling Range °C./mm | Elemental Composition, % Calcd. C | H | S | Found C | H | S |
|---|---|---|---|---|---|---|---|---|---|---|---|---|
| 1 | 12 | $C_{21}H_{36}SO_3$ | 368.5 | 371 | 83.5 | 160-164/0.1 | 68.44 | 9.85 | 8.70 | 69.86 | 9.52 | 7.80 |
| 2 | 9 | $C_{18}H_{30}SO_3$ | 326.5 | 337 | 73 | 137-142/0.05 | 66.22 | 9.26 | 9.82 | 67.26 | 9.38 | 7.78 |
| 3 | 15 | $C_{24}H_{42}SO_3$ | 410.6 | 426 | 74 | 190-192/0.2 | 70.20 | 10.31 | 7.81 | 71.13 | 10.39 | 7.59 |
| 4 | 18 | $C_{27}H_{48}SO_3$ | 452.7 | 458 | 52 | 210-215/0.1 | 71.63 | 10.69 | 7.08 | 72.10 | 10.66 | 5.83 |

TABLE II

Yields, Physical and Analytical Data of Methyl Higher Alkyl Benzene Sulfonate Esters $$C_nH_{2n+1}\text{-}\bigcirc\text{-}SO_3Na + (CH_3O)_2SO_2 \longrightarrow C_nH_{2n+1}\text{-}\bigcirc\text{-}SO_3CH_3 + CH_3OSO_3Na$$

| Ex. No. | Alkyl Type & n | Summary Formula | Molecular Weight Calcd. | Molecular Weight Found | Glc. Yield,% | Boiling Range °C./mm | Elemental Composition, % Calcd. C | H | S | Found C | H | S |
|---|---|---|---|---|---|---|---|---|---|---|---|---|
| 5 | i-15 | $C_{22}H_{38}SO_3$ | 382.58 | 383 | 83.5 | 165-180/0.1 | 69.07 | 10.01 | 8.38 | 69.25 | 10.07 | 7.54 |
| 6 | i-24 | $C_{31}H_{56}SO_3$ | 508.83 | 501 | — | 204-211/0.05 | 73.13 | 11.09 | 6.30 | 73.78 | 10.78 | 6.50 |
| 6 | i-30 | $C_{37}H_{68}SO_3$ | 593.0 | 597 | | 212-230/0.05 | 74.94 | 11.56 | 5.41 | 76.87 | 11.54 | 4.61 |

TABLE II-continued
Yields, Physical and Analytical Data of Methyl Higher Alkyl Benzene Sulfonate Esters $$C_nH_{2n+1}\!-\!\!\bigcirc\!\!-\!SO_3Na + (CH_3O)_2SO_2 \longrightarrow C_nH_{2n+1}\!-\!\!\bigcirc\!\!-\!SO_3CH_3 + CH_3OSO_3Na$$

| Ex. No. | Alkyl Type & n | Summary Formula | Molecular Weight Calcd. | Molecular Weight Found | Glc. Yield,% | Boiling Range °C./mm | Elemental Composition, % Calcd. C | Calcd. H | Calcd. S | Found C | Found H | Found S |
|---|---|---|---|---|---|---|---|---|---|---|---|---|
| 7 | 1-20 | $C_{27}H_{48}SO_3$ | 453 | 476 | — | 212–228/0.1 | 71.63 | 10.69 | 7.08 | 69.88 | 11.58 | 6.14 |

EXAMPLE 1

Methyl i-Dodecyl o-Xylene Sulfonate

The sodium i-dodecyl o-xylene sulfonic acid salt starting material of this ester was prepared by the known alkylation of o-xylene with propylene tetramer to yield higher alkyl o-xylenes. The latter had the following carbon number distribution in weight percentages according to mass spectroscopic analyses: $C_{10}$, 2.3; $C_{11}$, 18.6; $C_{12}$, 88.0; $C_{13}$, 12.0; $C_{14}$, 3.3 and $C_{15}$, 0.6. It should be noted that in this and subsequent examples, the determination of the carbon number of alkyl substituents was made by glc and/or mass spectroscopy analysis of the hydrocarbon precursor of the acid or salt. These data average to a $C_{12}$ olefin. This in turn means that the product of alkylating o-xylene with this olefin is, on an average, i-dodecyl o-xylene. The latter in turn is sulfonated to provide various isomeric i-dodecyl o-xylene sulfonic acids. One of the isomeric products is 4-i-dodecyl o-xylene sulfonic acid. The structural formula of this isomer is selected to represent the isomeric mixture of acids. This formula is also used for representing the derivatives, e.g.

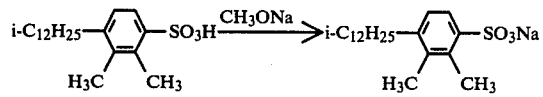

and other sulfonates derived via reactions of various higher olefins with o-xylene.

The i-dodecyl o-xylene sulfonic acid reactant had an 88% active content. It contained about 9% unreacted dodecyl o-xylene and 0.7% sulfuric acid plus about 2% water. This reactant, 897 g (containing 2.23 m sulfonic acid and 0.064 m sulfuric acid) was diluted with methanol to provide a 50 wt. by wt. percent solution. To the stirred solution of the sulfonic acid, 547 g of 25% sodium methoxide (2.53 m) solution was added slowly to produce the sodium sulfonate in an instantanoues reaction. Most of the methanol was then removed by distillation in water vacuum at about 30 mm. Thereafter, 2500 g xylene was added to facilitate the subsequent codistillation of methanol and water at atmospheric pressure. The high temperature of atmospheric distillation was important for the quantitative removal of the water. Distillation was continued until about 1000 g xylene solution of the anhydrous sodium sulfonate intermediate was obtained.

The sodium i-dodecyl o-xylene sulfonate solution was diluted to a total of 2952.8 g containing about 839.32 g (2.23 m) of reactant. This solution was placed into a 5 liter four necked round bottom flask, equipped with a thermometer, a mechanical stirrer, a dropping funnel, a reflux condenser and a nitrogen bubbler. The solution was then heated to about 140° and at that temperature with efficient stirring 429.8 g (3.41 m) of dimethyl sulfate was added to it during the course of 25 minutes. Stirring and heating at 140° were continued for 6 hours. During the reactant addition a gel was formed, this was completely broken in the course of the subsequent heating with the concurrent formation of a crystalline methylsulfuric acid sodium salt precipitate.

After standing overnight, the reaction mixture was filtered with suction using a Buchner funnel at room temperature in a nitrogen dry box. The filter cake was washed with toluene three times, using a 130 ml portion of toluene each time. The combined filtrates were then distilled to remove the hydrocarbon solvent. The crude residual product was 900 g. The theoretical amount of the methyl sulfonate is 821.9 g (2.23 m).

The residual product was fractionally distilled in vacuo. As the main distillate fraction 686 g (83.5%) yield of methyl i-dodecyl o-xylene sulfonate was obtained in 99.5% glc purity as a yellow viscous liquid boiling between 160°–164° at 0.1 mm. Prior to this fraction about 100 g of a forerun fraction containing about 54 g sulfonate (6.5% yield) was obtained. The distillation residue (50 g, 6%) was essentially pure sulfonate according to glc. Accordingly, the total product yield was about 96%.

The number average molecular weight of the main distillate determined in benzene by the osmotic method, was 371. This value is in fair agreement with the calculated molecular weight of methyl dodecyl xylene sulfonate, 368.5. The elemental composition of the product is shown in Table I.

EXAMPLE 2

Methyl i-Nonyl o-Xylene Sulfonate

For the preparation of the sodium i-nonyl o-xylene sulfonic acid starting material of this ester, the corresponding monoethanol ammonium salt was used. This was of about 85% purity and had a molecular weight of 373. About 95% of the higher alkyl substituents had nine carbon atoms. Also present was 3% with less than $C_9$ substituents and 2% $C_9$ plus. As impurities, about 13% higher alkyl xylenes and about 0.7% monoethanol ammonium sulfate, $(HOCH_2CH_2NH_3)_2SO_4$, and 1% water were present.

A 50% methanolic solution of 525 g of the above 85% monoethanol ammonium i-nonyl o-xylene sulfonate salt, containing 446 g (1.19 mole) of the compound, was prepared. To the stirred solution, 276.5 g of 25% methanolic sodium methoxide, having an equivalent amount of base, 1.28 mole, was added slowly to displace the amine base:

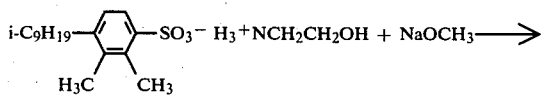

-continued

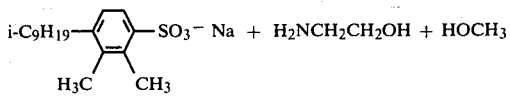

The resulting mixture was then distilled to remove the methanol and water while 300 g xylene and 225 g octylbenzene were slowly added to it. The distillation at atmospheric and then at 40 mm pressure was continued until the xylene, the monoethanolamine and octylbenzene were also removed. The found residual sodium sulfonate intermediate was 550 g. The calculated amount of sodium sulfonate is 398 g (1.19 m). This was dissolved in 700 g hot xylene and further utilized as an intermediate.

To the xylene solution of the above sodium i-nonyl o-xylene sulfonate salt intermediate was added 172.6 g (1.37 mole) of dimethyl sulfate at 140°, during 40 minutes in the manner described in the previous example. After a subsequent 6 hours heating at 140°, the reaction mixture was filtered under $N_2$ with suction and washed with five 140 ml portions of toluene. The combined filtrates were distilled to remove the hydrocarbons. This resulted in 410 g of a residual sulfonate product of a 90% purity by gas liquid chromatography. The latter corresponds to a yield of 369 g (95% of methyl sulfonate).

To remove the acidic and other water soluble impurities, a 10% hexane solution of the above residue was filtered and washed four times with 200 ml 5% sodium hydrogen carbonate solution. Thereafter, it was dried over 400 g anhydrous sodium sulfate, filtered and stripped from the hexane and other hydrocarbons. The thus extracted neutral product was 376 g of about 97% purity [i.e. it contained 365 g (94%) product].

Distillation of the above product at 0.2 mm resulted in a 45 g (12%) forerun of about 50% nonylxylene content, a 308 g (82%) of main sulfonate ester distillate and boiling between 145°–172° and 0.20–0.25 mm and a 23 g (6%) residue. Although the main yellow, viscous liquid fraction was pure by glc, it turned green on standing. Consequently, it was redistilled to yield 283 g (73%) of stable viscous yellow pure (100%) methyl i-nonyl o-xylene sulfonate having the properties shown in Table I.

EXAMPLE 3

Methyl i-Pentadecyl o-Xylene Sulfonate

The sodium i-pentadecyl o-xylene sulfonic acid salt starting material was prepared from the corresponding monoethanol ammonium salt. The latter was of 85% purity and had an average molecular weight of 460. The percentage distribution of the higher alkyl chains was 91%, $C_{15}$; 5%, $C_{15}$ minus; 4%, $C_{15}$ plus. The impurities were 14% pentadecyl xylene, 0.7% water and 0.3% amine sulfate.

About 518 g of the above 85% ammonium sulfonate (0.96 mole) was reacted with an acid equivalent amount of sodium methoxide in methanol in a manner described in the previous example. After the usual workup, 521 g of crude sodium sulfonate was obtained. The calculated amount of 100% sulfonate is 402.67 (0.96 mole).

The crude sodium i-pentadecyl o-xylene sulfonic acid salt was reacted with 163 g (1.29 mole, 34% excess) of dimethyl sulfate at about 136° C., in the manner described in the previous example. Thereafter the sodium methyl sulfate was removed by filtration in the usual manner. The filtrate was then stripped and the residual product was purified by washing in the usual manner. Distillation of the neutral product resulted in 292 g (74%) of a yellow viscous liquid main distillate, boiling between 190°–192° at 0.2 mm. This distillate was 98.6% pure methyl sulfonate ester. The last distillate was obtained with a slight decomposition between 192° and 213° at 0.2–0.3 mm as 38.2 g (9.7%) of an orange liquid of similar composition. The residue (8.8 g) was a largely solid black product of apparent decomposition. A distillate forerun of 19 g was also obtained which contained 12 g (3% of the total) of the sulfonate ester product.

The analytical data of the main distillate are shown in Table I.

EXAMPLE 4

Methyl i-Octadecyl o-Xylene Sulfonate

Monoethanol ammonium i-octadecyl o-xylene sulfonate salt of 85% purity and average molecular weight of 499 was used as a starting material. Its higher alkyl chain distribution was 95% $C_{18}$ and 5% $C_{15}$. As impurities, it contained about 14% octadecylbenzene, 0.3% ethanolammonium sulfate and 0.5% water. In the manner, described by Example 3, 415 g of this product (0.7058 m) was reacted with a total acids equivalent amount of sodium methylate to produce the desired sodium i-octadecyl o-xylene sulfonate salt intermediate.

The crude sodium salt was reacted with 120.2 g (0.954 m, 35% excess) of dimethyl sulfate at 142° in the usual manner. After 2 hours postaddition heating, the sodium methyl sulfate formed was filtered off as usual.

The filtrate was then concentrated, and washed as usual to remove acidic impurities. The crude product was then distilled in vacuo at about 1 mm with decomposition. The distillate was then refractionated at 0.1 mm without decomposition to yield 166.5 g (52%) of the product between 210° and 215° C.

EXAMPLE 5

Methyl i-Pentadecyl Benzene Sulfonate

The sodium i-pentadecyl benzene sulfonic acid salt starting material was prepared from the corresponding free acid mixture sold by the Stepan Chemical Co. under the trade name Petrostep A-70. This acid contains about 95% sulfonic acid, 1.5% sulfuric acid and 0.5% water. Its molecular weight is 370 (Calcd. mol. wt. 368.56). The alkyl chain distribution is $C_{10}$, 1.3; $C_{11}$, 4.4; $C_{12}$, 2.4; $C_{13}$, 2.0; $C_{14}$, 5.7; $C_{15}$, 67.2; $C_{16}$, 9.2; $C_{17}$, 3.7; $C_{18}$, 3.0. The average molecular weight of the alkylbenzene intermediate is 365. The weighted average alkyl chain length was about 14.7.

In the manner described in Example 1, 1163.9 g of the above 95% product (3 m sulfonic) acid was reacted with a total acids equivalent amount of sodium methoxide, 181.22 g (3.356 m) in methanol to prepare its anhydrous sodium salt. The latter was reacted in xylene with 505.7 g (4 m, 25% excess) of dimethyl sulfate, isolated by filtration, washing of the by-product with toluene, and the distillation of the solvents from the combined filtrates.

The residual product 1143 g was diluted with n-hexane to provide a 20% solution which was filtered, washed three times each with 650 ml 5% aqueous sodium hydrogen carbonate solution and dried over 562 g anhydrous sodium sulfate. Thereafter, the hexane was distilled off to leave 1100 g (96%) of crude neutral residual ester. Distillation of the latter provided 959 g (83.5%) of glc nominal methyl i-pentadecyl sulfonate ester as a yellow viscous liquid boiling between 165° and 180° at 0.1 mm and having an average molecular weight of 383. These data are summarized and the elemental composition is shown by Table II.

Example 6

Methyl i-Tetracosyl Benzene Sulfonate

The starting material for the preparation of the sodium i-tetracosyl benzene sulfonic acid intermediate was the corresponding sulfonic acid product SA 119 of Esso Chimie, France. This acid is produced via the sulfonation of a 350 number average molecular weight i-alkyl benzene obtained from the alkylation of benzene with a propylene oligomer of the corresponding glc percentage distribution: $C_{12}$, 0.7; $C_{15}$, 2.6; $C_{18}$, 8.8; $C_{21}$, 18.6; $C_{24}$, 27.4; $C_{27}$, 24.3; $C_{30}$, 11.5; $C_{33}$, 3.1; $C_{33+}$, 3.

The above sulfonic acid was 86% active and had an average molecular weight (mw) of 480. It also contained 0.25% sulfuric acid and 1.2% water. As starting material, 1116.3 g (2 m based on above mw) of the product was reacted with an acid equivalent amount of sodium methoxide (2.058 m) in methanol in a manner described in Example 1.

The resulting sodium sulfonate intermediate was reacted in 1500 ml xylene with 337.68 g (2.68 m, 34% excess) dimethyl sulfate. The addition of the sulfate (during the course of 30 minutes) at 140°, was followed by 8 hours heating at the same temperature. Thereafter the sodium methylsulfate by product was removed by filtration and the excess reactant and solvents by distillation as usual. The residual product was then washed as described in the previous example and yielded 979 g (96%) neutral liquid residual product.

Distillation of the crude product in the 0.3 to 3.0 mm pressure range occurred with decomposition and yielded a total 604 g (59%) of distillate fractions boiling between 200° and 280°. Redistillation was then carried out without decomposition at 0.1 mm to yield light yellow viscous light fractions boiling between 200° and 240° with molecular weights ranging from 459 to 600. The distillate fraction in the methyl tetracosyl sulfonate range boiled between 204°-211° at 0.05 mm and had a molecular weight of 501. Its elemental composition is shown in Table II. Another fraction in the methyl tricosyl sulfonate range distilled between 212°-230° at 0.05 mm and had a molecular weight range of 597. The elemental composition of this fraction is also shown in Table II.

Example 7

Methyl 1-Eicosyl Benzene Sulfonate

As an intermediate for this ester, the sodium salt of 1-eicosyl benzene sulfonic acid obtained from Continental Oil Co. was used. The eicosyl benzene precursor of this product was prepared from the 1-eicosene and benzene. The alkyl chain distribution was the following: $C_{18}$ minus, 7; $C_{18}$, 8; $C_{20}$, 50; $C_{22}$, 18; $C_{24}$, 5; $C_{26}$, 1; $C_{38,40,42,44}$, 11. The product contained about 10.5% eicosyl benzene and 2.8% sodium sulfate as impurities.

The aqueous sodium sulfonate was first mixed with xylene and later with octyl benzene and dehydrated by distillation. The anhydrous sulfonate, 277 g active compound (0.51 m on the basis of the average molecular weight of 540), was reacted in 586 g xylene with 94.5 g (0.75 m) of dimethyl sulfate at 140° for 6 hours in the usual manner. Then it was filtered and the filtrate stripped to obtain 328 g (61%) of crude residual ester product. Apparently, major amounts of the ester remained adsorbed on the solid sodium methyl sulfate by-product. The dry weight of the latter was 128.5 g, instead of the calculated 75 g.

The residual product was dissolved in seven and a half fold amount of hexane and washed with three portions of 5% aqueous sodium hydrogen carbonate solution, 153 ml each. The hexane solution was then dried over 214 g anhydrous sodium sulfate. The solvent as then removed by distillation to yield 328 g (61%) neutral residual product. Fractional distillation of the latter occurred with decomposition and yielded a total of 148 g of distillate liquids between 145°-276° under 0.6 to 4 mm pressure and 115 g of a mostly solid black residue. The middle distillate fraction, 114.5 g, a brown liquid was redistilled to provide 60 g of clear, yellow liquid methyl eicosyl sulfonate product between 212°-228° at 0.1 mm. As it is shown by the analytical data of Table II, this distillate had a molecular weight and elemental composition in fair agreement with the calculated values. Analyses of the foreruns of the second distillation by glc and for elemental composition showed that they consisted mainly of hydrocarbons, apparently produced by cracking.

EXAMPLE 8

Methyl Di-1-undecyl Benzene Sulfonate

The starting material of this experiment was derived from the residual product of benzene alkylation with n-undecene. This alkylate bottom was largely diundecyl benzene. The percentage carbon number distribution of the alkyl substituents was $C_{10,11}$, 56.6; $C_{12}$, 33.2; $C_{13}$, 10.2.

The sodium sulfonate derivative of this product was obtained from Continental Oil Co. as Conoco N5B. It contained 53.4% active sulfonate of 360 molecular weight and 4.2% hydrocarbons in water. The crude aqueous sodium sulfonate, 1308 g (1.94 m) was azeotroped with 1616 g of xylene to obtain a xylene solution of the anhydrous salt. This residue (1700 g) was diluted to provide 3000 g xylene solution of the reactant which was reacted with 329 g (2.61 m, 34.5% excess) dimethyl sulfate at 138° for 6 hours in the usual manner.

The crude reaction mixture was filtered with suction as in previous examples. The combined filtrates were then distilled to remove the solvents. The crude residual product (672 g, 72%) was extracted by vigorous shaking with 1832 g n-hexane. The undissolved residue was then similarly extracted with four 500 g portions each of n-hexane.

The combined hexane extracts were washed with three 320 ml portions each of 5% aqueous sodium hydrogen carbonate solution and then dried over 375 g anhydrous sodium sulfate. The hexane was then removed by distillation to yield 455 g (48.7%) of the crude neutral ester. The latter was distilled in high vacuo with decomposition to yield 290 g of a main distillate, between 213°-237° at 0.7-2.5 mm, and 67 g (7.2%) black, extremely viscous residue. The distillate was then redistilled without decomposition to provide 205 g (22%) of bis undecyl benzene sulfonic acid methyl ester, obtained as a clear yellow slightly viscous liquid between 177°-200° at 0.05 mm. The number average molecular weight of this product was found to be 475 by the osmotic method. The calculated molecular weight is 481.8.

Elemental Analysis-Calculated for $C_{29}H_{52}O_3S$: C, 72.45; H, 10.90; S, 6.67. Found: C, 74.03; H, 10.75; S, 6.01.

The hexane insoluble black liquid was dissolved in 1700 g toluene and was similarly washed, dried and distilled to provide 271 g (29%) of a residual product, which was found to be a sulfone by-product of the sulfonation of the alkylate bottoms starting material.

EXAMPLE 9

Ethyl i-Dodecyl o-Xylene Sulfonate

The sodium i-dodecyl o-xylene sulfonate starting material, 982.9 (2.61 m) was prepared in the manner described in Example 1. Then it was dissolved in 2000 g xylene and heated to the reaction temperature. To the stirred solution, 539.6 g (3.5 m) of diethyl sulfate was added at 138° during the course of 90 minutes. In a manner observed in the analogous reaction of dimethyl sulfate in Example 1, the reaction mixture gelled during the addition. The gel formed was broken up during the subsequent heating with the formation of the larger crystals of the sulfuric acid half ester sodium salt by product.

The reaction was completed by 5 hours heating at 138°–140° subsequent to the diethyl sulfate addition. The reaction mixture was then filtered and washed with toluene in the manner described in Example 1. Filtration was slow apparently due to the small size of the sodium ethyl sulfate by product crystals. The combined filtrates were then film evaporated and stripped in vacuo at 125° C. to remove the toluene and the excess diethyl sulfate. The crude residual product, 888 g (89%) was dissolved in 5000 g hexane, washed three times with 5% aqueous sodium hydrogen carbonate solution (380 ml each) in the usual manner to obtain the neutral product (885 g).

Fractional distillation of the product provided 545 g (54.8 g) of a hydrocarbon free yellow viscous liquid distillate heart cut boiling between 187°–191° at 0.35 mm with slight decomposition. The found molecular weight of this product, 387, was in agreement with the value calculated for ethyl i-dodecyl o-xylene sulfonate (382.6).

Elemental analyses: Calcd. for $C_{22}H_{38}SO_3$: C, 69.07; H, 10.01; S, 8.38. Found: C, 70.47; H, 9.86; S, 9.91.

EXAMPLE 10

Methyl i-Nonyl Naphthalene Sulfonate

The sodium i-nonyl naphthalene sulfonic acid salt starting material of this ester was prepared from experimental i-nonyl naphthalene prepared by King Industries, Inc. by the alkylation of naphthalene with isononene manufactured by Exxon Chemical via propylene isomerization. The reactions involved are indicated by the following scheme:

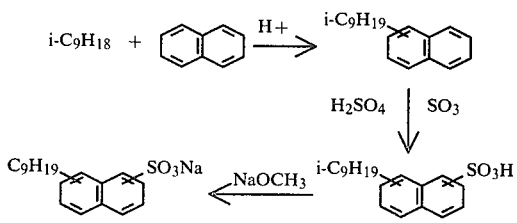

i-Nonyl naphthalene, 190 g (0.75 m) was sulfonated by adding 60.4 g (0.5 eq) of 96% sulfuric acid slowly to the stirred, ice cooled starting material at 2° C. during the course of 20 minutes. Then, to the resulting viscous, hazy, brown liquid, 22.94 g (0.25 acid eq) of chilled oleum was added in another 20 minutes at 5° C. with continued stirring and cooling. No visual change occurred during this second operation. However, after the stirring was discontinued, incomplete sulfuric acid reaction was indicated by the separation of a light, mobile hydrocarbon phase. Continuation of stirring the reaction mixture at room temperature over the weekend resulted in a stable homogeneous mixture of liquid i-nonyl naphthalene sulfonic acid and nonyl naphthalene.

The crude sulfonic acid was dissolved in 270 g methanol and neutralized with a 25% methanolic solution of sodium methoxide. About 69 g (1.28 m) of the base was required indicating that only about one third of the acid reacted.

The methanolic mixture of the sodium i-nonyl benzene sulfonate (and sodium sulfate by-product) was then distilled as usual, while xylene was being added to azeotrope the methanol and water. The concentration of the xylene of the resulting anhydrous mixture was adjusted so as to equal 250 g.

The main reaction, i.e., the methylation of the sodium sulfonate, was carried out in the usual manner to realize the following conversion.

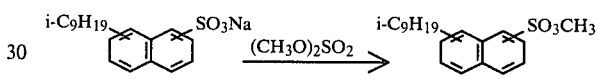

To the stirred sulfonate salt-xylene mixture, 163.8 g (1.3 m) of dimethyl sulfate was slowly added at 132°–140° C. in the course of 30 minutes. This resulted in a highly viscous, difficult to stir suspension. However, good stirring was obtained on the addition of 250 g xylene. Heating of the stirred mixture was continued at 140° for three hours. The reaction mixture was then allowed to cool and filtered with suction under nitrogen as usual. The filter cake was washed twice with 125 ml toluene each, then slurried with 450 ml toluene and filtered again. The combined filtrates were stripped at 85° C. at 0.1 mm to remove the toluene. A glc analysis of the resulting crude residual product (208 g) indicated that it contained 52% (108 g, 0.31 m) i-nonyl naphthalene and 43% (89.5 g, 0.26 m) methyl i-nonyl naphthalene sulfonate. This means that the overall conversion of the nonyl naphthalene to the sulfonate ester was 41%.

The residual product was distilled in vacuo using a simple Claisen distilling head. The overall distillate recovery of i-nonyl naphthalene plus its methyl sulfonate ester was good (91%). However, the separation of these two components was poor. Only 64 g (59%) of the sulfonate ester formed was isolated as an extremely viscous, yellow-greenish liquid.

Elemental analyses—calculated for $C_{20}H_{28}SO_3$: C, 68.93; H, 8.10; S, 9.20. Found: C, 69.47; H, 8.21; S, 8.78.

Molecular weight—calculated 348.5. Osmotic value found 354.

EXAMPLE 11

Methyl Di-i-Nonyl Naphthalene Sulfonate

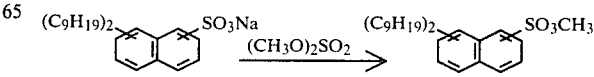

The sodium di-i-nonyl naphthalene sulfonic acid salt starting material was prepared from the corresponding free acid provided by King Industries, Inc. as a 39% heptane solution. At first, 1162 g of this solution, containing 453 g (0.985 m) of di-i-nonyl naphthalene sulfonic acid, was mixed with 1911 g xylene. Then the heptane and some of the xylene were distilled off to produce 2627 g of a xylene-sulfonic acid reactant solution. This solution was neutralized with 365.5 g of 15% methanolic sodium hydroxide solution which contains 0.137 m base, i.e., more than the theoretically required amount. The resulting mixture was then heated to distill off all the methanol and water.

The anhydrous distillation residue containing the sodium sulfonate reactant was diluted with further amounts of xylene to obtain a total of 1480 g of a mixture. To the latter, 166.3 g (1.32 m) of dimethyl sulfate was added at 137°–139° with stirring over the course of 15 minutes. Heating and stirring of the mixture was continued for 4½ hours to complete the reaction. The resulting mixture was then filtered as usual. For washing the filter cake, 12 portions of toluene, 50 ml each, were used. The combined filtrates were distilled to remove the solvents. The crude residual product obtained was 704 g (50% more than the theoretical amount, 467.5 g). Glc indicated that it was essentially the desired ester.

Distillation of the crude product in vacuo resulted in significant cracking. However, redistillation occurred without decomposition and provided 258 g (55%) pure di-i-nonyl naphthalene sulfonate. This distillate boils between 188° and 205° at 0.05 mm and is a clear yellow extremely viscous liquid.

Elemental analysis—calculated for $C_{29}H_{46}SO_3$: C, 73.37; H, 9.77; S, 6.75. Found: C, 75.23; H, 10.04; S, 5.96.

Molecular weight—Calculated 474.7. Osmotic value found 484.

What is claimed is:

1. Dialkyl benzene sulfonate esters of the formula

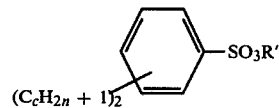

wherein R' is $C_1$ to $C_2$ alkyl; c is 9 to 50.

2. The compositions of claim 1 wherein R' is methyl.

3. Isomeric di-linear-alkyl benzene sulfonate ester compounds of the formula:

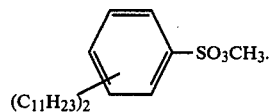

* * * * *